United States Patent [19]

Hasson

[11] Patent Number: 4,496,345
[45] Date of Patent: Jan. 29, 1985

[54] BALLOONED CANNULA

[76] Inventor: Harrith M. Hasson, 2043 N. Sedgwick, Chicago, Ill. 60614

[21] Appl. No.: 413,152

[22] Filed: Aug. 30, 1982

[51] Int. Cl.³ .......................................... A61M 25/00
[52] U.S. Cl. ................................... 604/103; 604/102
[58] Field of Search .................... 604/96, 97, 98, 103, 604/102, 101, 100

[56] References Cited

U.S. PATENT DOCUMENTS

| | | |
|---|---|---|
| 2,460,473 | 2/1949 | Smith . |
| 2,480,041 | 8/1949 | Myller . |
| 2,845,930 | 8/1958 | Brown . |
| 3,232,253 | 8/1966 | Di Palma ........................ 604/103 X |
| 3,385,301 | 5/1968 | Harautuneian . |
| 3,448,739 | 6/1969 | Stark et al. . |
| 3,547,126 | 12/1970 | Birtwell .............................. 604/102 |
| 3,865,666 | 2/1975 | Shoney ........................... 604/103 X |
| 3,965,909 | 6/1976 | Waddell et al. . |
| 3,970,089 | 7/1976 | Saice . |
| 3,978,863 | 9/1976 | Fettel et al. . |
| 3,985,601 | 10/1976 | Panagrossi ..................... 604/103 X |
| 3,991,767 | 11/1976 | Miller, Jr. et al. . |
| 3,996,938 | 12/1976 | Clark . |
| 4,029,104 | 6/1977 | Kerber . |
| 4,057,065 | 11/1977 | Thow . |
| 4,088,135 | 5/1978 | O'Neill . |
| 4,100,923 | 7/1978 | Southern . |
| 4,114,625 | 9/1978 | Onat . |
| 4,117,847 | 10/1978 | Clayton . |
| 4,122,858 | 10/1978 | Schiff . |
| 4,154,243 | 5/1979 | Parel et al. ...................... 604/100 |
| 4,222,384 | 9/1980 | Birtwell .............................. 604/103 |
| 4,341,210 | 7/1982 | Elam . |
| 4,341,217 | 7/1982 | Ferguson et al. . |

FOREIGN PATENT DOCUMENTS 325740 10/1902 France .

OTHER PUBLICATIONS

"Ballooned Uterine Elevator Cannula", Hasson, H. M., *Amer. Journal of Obstetrics and Gynecology*, vol. 123, No. 6, pp. 658–659, Nov. 15, 1975.

"Effective Uterine Fundal Elevation in Laparoscopy", Hasson, H. M., *The Journal of Reproductive Medicine*, p. 76 Editorial Page, 1975.

"A Modified Ballooned Uterine Elevator Cannula", Hasson, H. M., *The Journal of Reproductive Medicine*, vol. 25, No. 2, pp. 72–74, Aug. 1980.

Primary Examiner—Stephen C. Pellegrino
Attorney, Agent, or Firm—Wood, Dalton, Phillips, Mason & Rowe

[57] ABSTRACT

A ballooned cannula including an elongated tube encompassed by a housing formed of a biologically inert, soft plastic. A balloon is formed on one end of the tube and the housing by a tip structure including radially inner and outer sleeves, the inner sleeve including a shoulder against which the tube end may abut and the outer sleeve defining the balloon. The cannula also includes an integral handle formed of flexible material including a flexible injection receiver.

7 Claims, 6 Drawing Figures

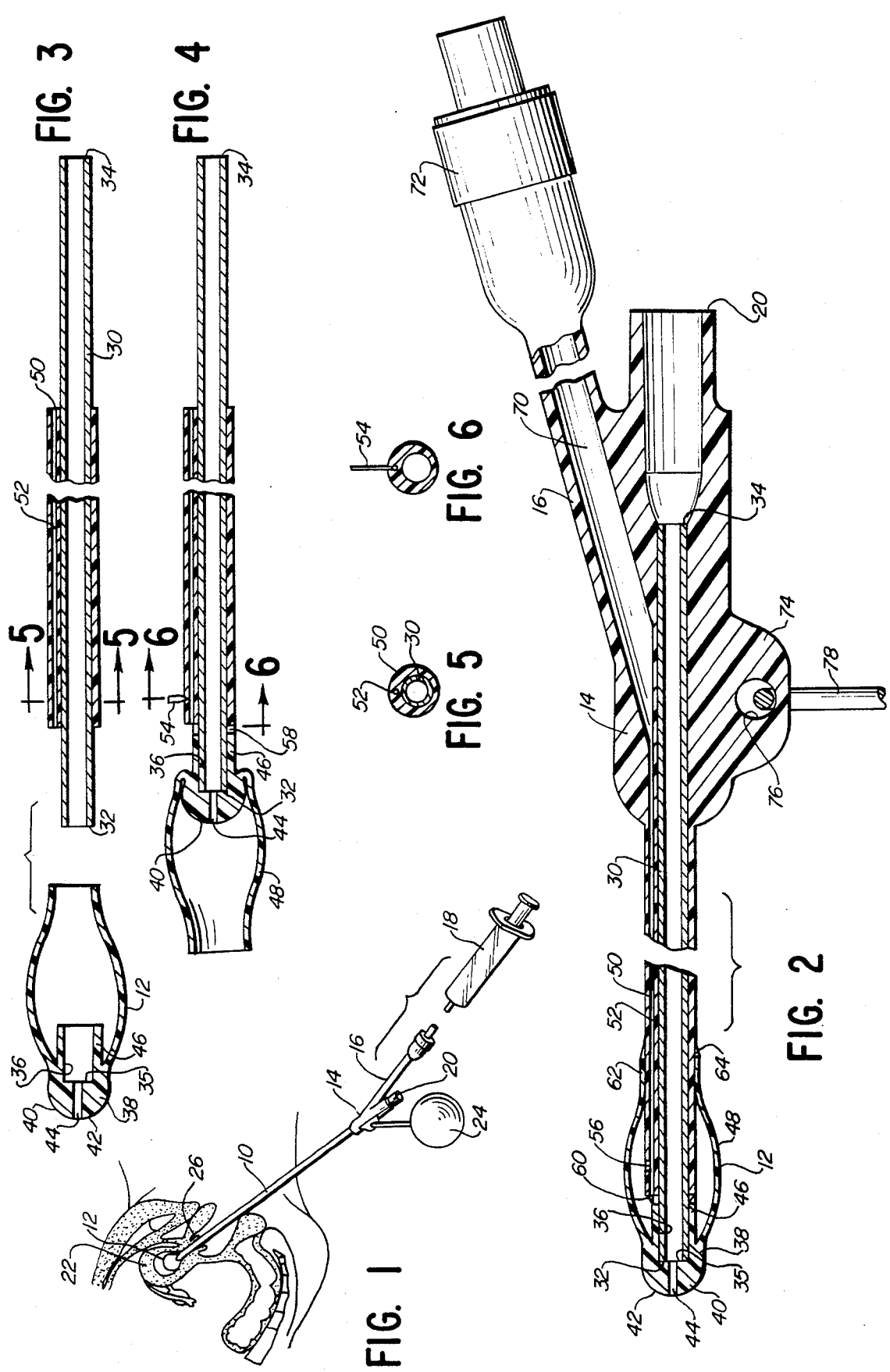

BALLOONED CANNULA

FIELD OF THE INVENTION

This invention relates to a ballooned cannula, and more particularly, a ballooned cannula that may be advantageously employed in procedures requiring uterine elevation.

BACKGROUND ART

Prior art of possible relevance includes the following U.S. Pat. Nos. 3,948,270 issued Apr. 6, 1976 to Hasson; 3,965,909 issued June 29, 1976 to Waddell et al; 3,978,863 issued Sept. 7, 1976 to Fettel et al; 4,029,104 issued June 14, 1977 to Kerber; 4,057,065 issued Nov. 8, 1977 to Thow; and 4,089,337 issued May 16, 1978 to Kronner et al; of which patents 3,948,270 and 4,089,337 are believed to be the most pertinent.

In my above identified patent there is disclosed a novel uterine cannula which is useful in a variety of gynecological procedures wherein uterine elevation or manipulation and/or uterotubal injection are indicated. Reference may be had to my patent for a specific identification of the nature and types of such procedures.

Considerable experience with the uterine cannula described in my prior patent illustrates that the same works extremely well for its intended purposes, suffering only minor inconveniences. For example, the rigid injection receiver therein disclosed and the nature of the handle utilized in the device are such that leakage is occasionally encountered. It is also desirable to provide a more positive cushioning of the cannula tip. Occasionally, due to the rigid nature of the injection receiver, when coupled to the tip of a syringe, relative motion between the two during use can cause breakage of the syringe tip.

Finally, the number of parts employed in my patented construction increases the cost of its manufacture.

The present invention is an improvement of my previously patented uterine cannula and intended to overcome one or more of the above problems.

SUMMARY OF THE INVENTION

According to one aspect of the invention there is provided an elongated tube having two spaced ports in communication with each other via the interior of the tube. A housing formed of a biologically inert, soft plastic material surrounds the tube along the length thereof and has an end disposed such that at least one end of the tube extends from the housing. The housing includes an inlet in fluid communication with one of the ports, a pressurizing conduit extending to substantially the housing end, and a pressurizing port in fluid communication with the conduit. A biologically inert, expandable balloon is secured to the tube end and is comprised of a radially inner sleeve disposed about the tube end and a radially outer sleeve of thin construction connected and sealed to the housing near the housing end. A smooth tip interconnects the sleeves adjacent the end of the tube and has an outlet in fluid communication with the other of the ports of the tube. The interface of the sleeves is in fluid communication with the pressurizing conduit.

In a preferred embodiment of the invention, the housing is assembled onto the tube.

In another aspect of the invention, the housing further defines a flexible injection receiver in fluid communication with the interior of the tube.

Preferably, the balloon tip has a recess defined by the sleeve for receiving the end of the tube and the recess, together with the outlet define a shoulder against which the tube end is abutted.

In a highly preferred embodiment, the radially outer sleeve is constructed and arranged so it can be reverse folded away from the radially inner sleeve to allow the tube to be inserted into the previously mentioned recess during assembly of the cannula.

Other objects and advantages will become apparent from the following specification taken in connection with the accompanying drawings.

DESCRIPTION OF THE DRAWINGS

FIG. 1 is a somewhat diagramatic view illustrating a ballooned cannula made according to the invention disposed within the uterus of a patient to provide uterine elevation;

FIG. 2 is an enlarged, sectional view of the cannula;

FIG. 3 is a sectional view of a portion of the cannula at a stage during the assembly thereof;

FIG. 4 is a view similar to FIG. 3 but showing a subsequent stage in the assembly;

FIG. 5 is a sectional view taken approximately along the line 5—5 in FIG. 3; and FIG. 6 is a sectional view taken approximately along the line 6—6 in FIG. 4.

BEST MODE FOR CARRYING OUT THE INVENTION

An exemplary embodiment of a ballooned cannula made according to the invention is illustrated in one intended application in FIG. 1. The cannula includes an elongated shaft 10 terminating in a balloon tip 12. The end of the shaft 10 opposite the balloon tip 12 is provided with a handle 14 whereby the entire cannula may be manipulated. One part of the handle 14 includes a pressure fluid entrance 16 which is adapted to be associated with a syringe 18 or the like. Introduction of fluid by the syringe 18 is operable to expand the balloon 12.

The handle 14 also includes an injection receiver 20 which may be associated with a suitable syringe (not shown) whereby fluid may be injected through the shaft 10 into the interior of a body cavity as, for example, a uterus 22.

The handle 14 may also removably receive a weight 24 which serves to elevate the uterus 22 when the cannula is properly disposed therein. The weight 24 also serves to cause the expanded balloon 12 to seal the uterus 22, and prevent retrograde leakage of the injected fluid or air.

In use, the cervix 26 is exposed and grasped with a suitable instrument as, for example, a tenaculum (not shown). Appropriate uterine dimensions are then determined utilizing a sound as is well known in the art. The cannula, with the balloon 12 deflated, is then inserted into the uterus until the uterine fundus is touched. The syringe 18 is then applied to the cannula to inflate the balloon 12, normally with air. Typically, 4–10 milliliters of air are employed. Of course, if resistance if felt prior to the completion of the injection of the desired amount of air, further injection of air is ceased.

Once the balloon 12 is inflated, the inflation syringe 18 is removed and withdrawal of the cannula from the uterine cavity is gently attempted. Resistance to such withdrawal indicates that the cannula is properly placed and then the weight 24, typically 200 grams, is attached. The weight seals the uterus and elevates the same anteriorly. Where further uterine mobilization is required, the handle 14 may be grasped and moved appropriately.

Uterotubal injection, where required, is accomplished by the introduction of a syringe into the injection receiver 20 in the usual case. However, extension tubing (not shown) may be interposed between the injection receiver 20 and a syringe provided of course that the tubing is primed with fluid to be injected to avoid the introduction of air.

Turning now to FIG. 2, the cannula will be described in greater detail. The shaft 10 is defined by a cylindrical tube 30 formed of a malleable stainless steel of the same type employed in the manufacture of intravenous needles or cannulae. This constructional feature allows the shaft 10 to be bent to conform to the uterine axis where required.

The tube 30 has opposed ends 32 and 34 with the end 32 defining an outlet port and the end 34 defining an inlet port. The end 32 abuts against a shoulder 35 within a recess 36 in one side of the base 38 of the cannula tip 40. The opposite side of the base 38 is smoothly rounded as at 42 and centrally of the base 38 is a small passage 44 of considerably lesser diameter than that of the recess 36. In this respect, the recess 36 has a diameter equal to or slightly less than the outside diameter of the tube 30 so that the latter may be snugly received and fastened therein. The passage 44 is of reduced diameter to assure the presence of the shoulder 35. The tip 40 is made of a biologically inert resilient plastic material as, for example, medical grade silicone. This insures that all contact of the tip 40 with the interior of the uterus 22 will be cushioned. At the same time, the presence of the shoulder 35 assures that the end 32 of the tube 30 cannot be inadvertently extended through the passage 44 thus the tube end 32 could never contact the uterine wall during use.

The recess 36 is defined by a radially inner sleeve 46 integral with the base 38 of the tip 40. Also integral with the base 38 is a radially outer sleeve 48 which is somewhat thinner than the sleeve 46 and which has a greater axial length. The sleeve 48 defines the balloon 12 as will be seen.

The tube 30, intermediate its ends, is surrounded by an elongated housing 50 (FIG. 3) formed of a biologically inert plastic material, again, preferably medical grade silicone. The housing 50 is assembled onto the tube 30 and includes an axial, elongated passage 52 exterior of the tube 30. The passage 52 is employed to direct pressurized fluid to the interior of the sleeve 48 for the purpose of inflating the balloon 12.

As seen in FIGS. 4 and 6, during assembly of the cannula, a tool 54 is brought into contact with the housing 50 in alignment with the passage 52 to form a radially directed aperture 56 (FIG. 2). This aperture 56 is formed in the housing 50 near its end closest to the tube end 32.

With the outer sleeve 48 reverse folded as best seen in FIG. 4, the tube end 32 is then inserted into the recess 36 until the shoulder 35 is abutted. Preferably, the arrangement is such that a small annular gap 58 exists between the end of the inner sleeve 46 and the end of the housing 50. A suitable adhesive and/or solvent weld 60 is formed at the gap 58 to unite the tip 40 and the housing 50. Because of the previously formed radial passage 56, this union does not require extreme caution to avoid plugging the end of the passage 52.

The radially outer sleeve 48 may then be rolled over the housing past the port 56 to the position illustrated in FIG. 2 and the end 62 of the sleeve 48 sealed to the housing 50 by suitable adhesive or a solvent weld 64.

The handle 14 is then formed, as by molding, on the tube 30 and the housing 50 at the righthand end thereof as viewed in the drawings. Preferably the housing 14 is again formed of a biologically inert plastic material such as medical grade silicone such that when formed, it will be indistinguishable from the housing 50 and become a part thereof.

The handle 14 includes the inflation port 16 which is defined by an interior conduit 70 in fluid communication with the axial passage 52 in the housing 50. The end of the conduit 70 remote from the passage 52 mounts a conventional pressure valve 72 to which the inflation syringe 18 may be removably secured.

The end 34 of the tube 30 is contained within the handle 14 and in fluid communication with the injection receiver 20. Because the housing 14 is formed of a flexible plastic, it will be appreciated that relative movement between the cannula and an injection syringe received in the receiver 20 can occur without damage to either.

Finally, the handle 14 includes an integral tab 74 provided with an aperture 76 which may receive a hook 78 attached to the weight 24 for the purposes previously described.

From the foregoing, it will be appreciated that a cannula made according to the invention posesses several advantages over those heretofore known. As just alluded to, relative movement between an injection syringe and the cannula can occur without damage to either by reason of the flexible nature of the injection receiver 20. The unique construction of the tip 40 positively assures cushioned contact of the cannula end with the fundus of the uterus to prevent uterine perforation. The flexible nature of the injection receiver along with the fact that the handle 14 is integral with the cannula avoid leakage problems heretofore encountered with other structures.

I claim:

1. In a ballooned cannula, the combination of an elongated tube having two spaced ports in fluid communication with each other via the interior of the tube;

a housing formed of a biologically inert, soft plastic material surrounding said tube along the length thereof and having an end disposed such that at least one end of said tube extends from said housing, said housing including
an inlet in fluid communication with one of said ports, a pressurizing conduit extending to substantially said housing end, and a
pressurizing port in fluid communication with said conduit and adapted to be connected to a source of pressurizing fluid; and a biologically inert, expandable one piece balloon secured to said tube one end and comprised of a radially inner integral sleeve disposed about said tube one end, a radially outer integral sleeve of thin construction connected and sealed to said housing near said housing end, and a smooth tip interconnecting said sleeves adjacent said tube one end and having an outlet in fluid communication with the other of said ports, the interface of said sleeves being in fluid communication with said pressurizing conduit, said radially inner sleeve having a lesser axial length than said radially outer sleeve, said other port being defined by an open end of said tube, and said outlet opening into the interior of said radially inner sleeve.

2. The ballooned cannula of claim 1 wherein said pressurizing conduit opens to said interface in the radial direction at a location spaced from said housing end.

3. The ballooned cannula of claim 1 wherein said tube is semi-rigid so as to be bendable and said housing is assembled onto said tube.

4. In a ballooned cannula, the combination of:
a metallic tube terminating in one end adapted to be inserted within a body cavity;
a balloon and protective tip for said tube one end and formed of a biologically inert, resilient plastic material, said balloon and tip being of unitary construction and including a base having a smoothly rounded surface on one side and an inner sleeve defining a recess on the opposite side sized and shaped to snugly receive said tube one end, a fluid passage of lesser dimension than said recess extending from the center of said recess through said base and opening to said base one side, said fluid passage and said recess defining an annular shoulder abutted by said tube one end, and a thin, outer sleeve integral with and extending generally axially from said base one side past said base opposite side in surrounding relation to said inner sleeve to terminate in an end surrounding said tube at a location between the ends thereof;
means for sealing said sleeve end to said cannula; and
means for introducing a fluid between said inner and outer sleeves to selectively expand the outer sleeve to cause the same to balloon.

5. The ballooned cannula of claim 4 wherein said tube is substantially contained by a biologically inert plastic housing assembled onto said tube, and said outer sleeve end is sealed to said housing; said introducing means comprising an axial passage within said housing.

6. The ballooned cannula of claim 4 wherein said outer sleeve is constructed and arranged so as to be reverse folded away from said base opposite side and about said base one side to allow said balloon and tip to be mounted on said tube one end during assembly of said cannula.

7. The ballooned cannula of claim 5 wherein said housing further defines a flexible injection receiver in fluid communication with the interior of said tube.

* * * * *